(12) United States Patent
Senderoff et al.

(10) Patent No.: US 6,790,439 B1
(45) Date of Patent: *Sep. 14, 2004

(54) THROMBOPOIETIN COMPOSITIONS

(75) Inventors: Richard I. Senderoff, Bellevue, WA (US); Kathleen M. Kontor, Bothell, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/486,451

(22) Filed: Jun. 7, 1995

(51) Int. Cl.[7] ............................................... C07K 14/52
(52) U.S. Cl. .................................................. 424/85.1
(58) Field of Search ........................... 424/85.1; 514/12

(56) References Cited

U.S. PATENT DOCUMENTS

| | | | |
|---|---|---|---|
| 4,637,834 A | | 1/1987 | Thurow ........................ 106/124 |
| 5,096,885 A | | 3/1992 | Pearlman et al. .............. 514/12 |
| 5,344,644 A | * | 9/1994 | Igari et al. ................... 424/85.1 |
| 5,358,708 A | * | 10/1994 | Patel ........................... 424/85.1 |
| 5,534,269 A | * | 7/1996 | Igari et al. ................... 424/489 |
| 5,580,856 A | * | 12/1996 | Prestrelski et al. ............ 514/21 |

FOREIGN PATENT DOCUMENTS

WO 94/03198 2/1994

OTHER PUBLICATIONS

Manning et al., Pharm. Res., vol. 6(11), pp. 903 to 918, 1989.*
McDonald et al., Exp. Hematol. 17: 865–871, 1989.
Hill et al., Exp. Hematol. 17: 903–907, 1989.
McDonald, Exp. Hematol. 16: 201–205, 1988.
Foster et al., Proc. Natl. Acad. Sci. U.S.A. 91: 13023–13027, 1994.
Wang et al., Journal of the Parenteral Drug Association 34: 452–462, 1980.

* cited by examiner

Primary Examiner—Lorraine Spector
(74) Attorney, Agent, or Firm—Deborah A. Sawislak (57) ABSTRACT

Compositions of thrombopoietin, methods of reducing adsorption of thrombopoietin to a surface, and methods of stabilizing a composition of thrombopoietin are disclosed. The compositions comprise, in addition to thrombopoietin, a physiologically acceptable buffer, a surface adsorption inhibitor selected from the group consisting of non-ionic surfactants and polyols, and an isotonic amount of a physiologically acceptable salt.

15 Claims, 5 Drawing Sheets

THROMBOPOIETIN COMPOSITIONS

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. Cytokine action results in cellular proliferation and differentiation, with a response to a particular cytokine often being lineage-specific and/or stage-specific. Development of a single cell type, such as a platelet, from a stem cell may require the coordinated action of a plurality of cytokines acting in the proper sequence.

Various cytokines have been developed as therapeutic agents. For example, erythropoietin, which stimulates the development of erythrocytes, is used in the treatment of anemia arising from renal failure. Several of the colony stimulating factors have been used in conjunction with cancer chemotherapy to speed the recovery of patients' immune systems. Interleukin-2, α-interferon and γ-interferon are used in the treatment of certain cancers.

An activity that stimulates megakaryocytopoiesis and thrombocytopoiesis has been identified in body fluids of thrombocytopenic animals and is referred to in the literature as "thrombopoietin" (recently reviewed by McDonald, *Exp. Hematol.* 16:201–205, 1988 and McDonald, *Am. J. Ped. Hematol. Oncol.* 14:8–21, 1992). This protein has now been produced using genetically engineered cultured cells. See, de Sauvage et al., *Nature* 369:533–538, 1994; Lok et al., *Nature* 369:565–568, 1994; Kaushansky et al., *Nature* 369:568–571, 1994; and Bartley et al., *Cell* 77:1117–1124, 1994.

Human thrombopoietin (TPO) is a 70 kD glycoprotein of 332 amino acid residues. It contains ah amino-terminal growth factor domain of approximately 152 residues and a carboxyl-terminal domain rich in carbohydrate. Truncated forms of TPO comprising the amino-terminal domain exhibit biological activity in vitro and in vivo. Non-human TPOs have also been described in the scientific literature (e.g., Lok et al., ibid.; Bartley et al., ibid.; Shimada et al., *Blood* 84 (10 Suppl. 1):326a, 1994).

Thrombopoietin appears to be subject to proteolysis and was isolated in heterogeneous or degraded form (Bartley et al., ibid.; de Sauvage et al., ibid.). Preparations of thrbmbopoietin reported in the scientific literature are therefore not well characterized as to composition and the relative activities of the various molecular species, although at least some of the proteolytic products are biologically active. However, little work has been reported to date on the large-scale production of thrombopoietin, and there is a need in the art for compositions of TPO that are suitable for pharmaceutical use. Such formulations should be stable on storage and easy to use.

SUMMARY OF THE INVENTION

It is an object of the present invention to provide pharmaceutical compositions of TPO, including aqueous compositions, that are stable on storage.

It is a further object of the invention to provide methods of reducing adsorption of TPO to surfaces, including surfaces of storage vials and filters used in the preparation and packaging of pharmaceutical compositions of TPO.

It is an additional object of the invention to provide methods for stabilizing pharmaceutical compositions of TPO, including aqueous solutions and lyophilized powders.

In one aspect, the present invention provides a composition comprising TPO, a physiologically acceptable buffer, a surface adsorption inhibitor selected from the group consisting of non-ionic surfactants and polyols, and an isotonic amount of a physiologically acceptable salt. The TPO may be human TPO or non-human (e.g., rat, mouse, dog or non-human primate) TPO. Within certain embodiments of the invention, the composition is an aqueous solution having a pH of 5.0 to 7.0, preferably 5.5 to 6.5. Within an alternative embodiment, the composition is a lyophilized powder. Within a further embodiment, the composition comprises histidine in an amount sufficient to reduce aggregation of the thrombopoietin. Within another embodiment, the composition is an aqueous pharmaceutical composition comprising thrombopoietin, 10–100 mM phosphate buffer, 0.01–1.0% polysorbate 20 or polysorbate 80, and an isotonic amount of sodium chloride, the composition having a pH of approximately 6.0.

Within another aspect, the present invention provides a method for reducing adsorption of thrombopoietin to a surface comprising adding to an aqueous solution of thrombopoietin an effective amount of a surface adsorption inhibitor selected from the group consisting of non-ionic surfactants and polyols prior to contacting the solution with the surface. Within selected embodiments of the invention the surface adsorption inhibitor is a polyoxyethylene sorbitan fatty acid ester, such as polysorbate 20 or polysorbate 80.

Within a third aspect, the present invention provides a method of stabilizing a composition of thrombopoietin comprising adding to the composition an effective amount of histidine.

These and other aspects of the invention will become evident upon reference to the following detailed description and the attached drawings.

DETAILED DESCRIPTION OF THE INVENTION

The term "isotonic" is used herein for its conventional meaning, that is a tonicity equal to that of blood, equivalent to a 0.9% solution of NaCl. "An isotonic amount" of a salt is that amount required to make a solution isotonic or to produce an isotonic solution upon reconstitution of a lyophilized preparation.

Concentrations are specified herein in units of molarity or % w/v of liquid compositions. When the composition is in the form of a lyophilized powder, the concentrations of the respective components will be such as to provide the specified concentration on reconstitution of the powder.

The compositions of the present invention are formulated to reduce the loss of TPO activity due to surface adsorption, aggregation, other physical or chemical degradation, or combinations of these processes. It has been found by the inventors that non-ionic surfactants and polyols can reduce the adsorption of TPO to surfaces, such as filters or vials.

According to the present invention, TPO is combined with a buffer, a surface adsorption inhibitor selected from the group consisting of non-ionic surfactants and polyols; and an isotonic amount of a physiologically acceptable salt. The composition may be formulated as an aqueous solution or a lyophilized powder. The latter is reconstituted prior to use with a pharmaceutically acceptable diluent, such as sterile water for injection.

Buffers for use within the present invention include low ionic strength, physiologically acceptable buffers that are effective within the pH range of 5.0–7.0. Such buffers include phosphate, acetate, citrate, succinate and histidine buffers. By "low ionic strength" is meant 5–500 mM, preferably 10–100 mM, most preferably about 20 mM. Sodium and potassium phosphate buffers and histidine buffer are preferred. It is preferred that the pH of the composition be from 5.5–6.5, most preferably about 6.0. A particularly preferred buffer is 20 mM sodium phosphate buffer, pH 6.0 (16 mM monobasic sodium phosphate +4 mM dibasic sodium phosphate).

Surface adsorption inhibitors useful within the present invention include non-ionic surfactants and polyols. Non-ionic surfactants include polyoxyethylene sorbitan fatty acid esters, such as polysorbate 20 (polyoxyethylene sorbitan monolaurate), polysorbate 80 (polyoxyethylene sorbitan monooleate), and the like. Other non-ionic surfactants useful in this regard include polyethylene oxides; sorbitan esters; polyoxyethylene alkyl ethers; and glycerides of fatty acids, including glyceryl monooleate and glyceryl monostearate. Polyols for use within the present invention include polyethylene glycol (e.g. PEG 3350), mannitol, xylitol, sorbitol, inositol, and glycerol. In general, the surface adsorption inhibitor will be included at a concentration from 0.001% to 5%, preferable 0.01% to 1.0%, more preferably about 0.05%. A particularly preferred surface adsorption inhibitor is polysorbate 80 at a concentration of about 0.05%. Combinations of surface adsorption inhibitors (e.g. polysorbate 80+PEG 3350) can also be used.

An isotonic amount of a physiologically acceptable salt has been found to further reduce surface adsorption of TPO when included in aqueous solutions containing a non-ionic surfactant. Preferred salts in this regard include chloride salts such as NaCl, KCl, $CaCl_2$ and $MgCl_2$. NaCl is particularly preferred. As will be evident to those skilled in the art, the actual amount of a salt required to achieve isotonicity will depend on such factors as the particular salt chosen and the other components of the composition.

Advantages may be obtained by including within the compositions combinations of certain components disclosed above. For example, the addition of histidine to a non-histidine-buffered composition can further stabilize TPO in the composition. Experimental evidence indicates that histidine reduces aggregation of TPO and may also reduce non-proteolytic degradation (e.g. deamidation or oxidation) at pH>5.5. Histidine may thus be included in, for example, a phosphate-buffered TPO composition at a concentration of 5–500 mM, preferably 10–100 mM, more preferably about 20 mM. Polyethylene glycol or another polyol may be added to a composition containing a non-ionic surfactant to further reduce surface adsorption. Histidine and polyols may be advantageously included in lyophilized compositions to reduce aggregation.

Albumin may also be included in the compositions of the present invention. Human serum albumin is preferred for inclusion in pharmaceutical compositions intended for human use, although non-human albumins may be used within reagent-grade compositions or those intended for veterinary use (including experimental use in animals). Albumin is useful as an excipient in lyophilized compositions and acts as a stabilizer when included at a concentration of 0.01–1.0%, preferably about 0.25%.

One or more preservatives may also be included in the compositions of the present invention, particularly in those compositions packaged for multiple use. Preservatives that can be used within the present invention include those commonly used in pharmaceutical preparations, such as methylparaben, propylparaben, benzyl alcohol, m-cresol, ethylmercurithiosalycilate, phenol, thimerosal, and the like.

Sugars may be included in the compositions of the present invention as bulking agents, stabilizers, or tonicity adjusters. Sugars are of particluar interest as bulking agents and stabilizers for lyophilized compositions. Suitable sugars include dextrose, lactose, maltose, sucrose, trehalose and the like.

Pharmaceutical compositions of TPO are formulated for parenteral, particularly intravenous or subcutaneous, delivery according to conventional methods. Methods of formulation are well known in the art and are disclosed, for example, in *Remington's Pharmaceutical Sciences*, Gennaro, ed., Mack Publishing Co., Easton Pa., 1990, which is incorporated herein by reference. In pharmaceutical compositions, the concentration of TPO will typically be within the range of 0.1 to 10 mg/ml, although more highly concentration solutions can be provided and diluted prior to use. Compositions having TPO concentrations outside this preferred range can also be prepared, such as for use as research reagents. Components in addition to those disclosed above may be included for purposes known in the art, for example bulking agents added prior to lyophilization. These compositions may further contain other cytokines, particularly early-acting cytokines such as stem cell factor, IL-3, IL-6, IL-11 or GM-CSF.

TPO compositions intended for pharmaceutical use will be sterile and pyrogen-free, and will be manufactured and packaged according to accepted pharmaceutical procedures. The compositions can be packaged in unit dosage or multiple dosage quantities. The compositions will typically be packaged in sealed glass vials with polytetrafluoroetylene-lined stoppers and with appropriate labeling. Lyophilized compositions may be packaged as a kit that includes an appropriate quantity of a suitable diluent, such as water for injection (WFI) or 5% dextrose in WFI.

Thrombopoietin compositions of the present invention can be used therapeutically wherever it is desirable to increase proliferation of cells of the myeloid lineage, such as in the treatment of cytopenia, such as that induced by aplastic anemia, myelodisplastic syndromes, chemotherapy or congenital cytopenias. TPO is particularly useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. TPO can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for TPO include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

Therapeutic doses will generally be in the range of 0.1 to 100 µg/kg of patient weight per day, preferably 0.5–50 µg/kg per day, more preferably 1–25 µg/kg/day, with the exact dose determined by the clinician according to accepted standards, taking into account the nature and severity of the condition to be treated, patient traits, etc. Determination of dose is within the level of ordinary skill in the art. TPO will commonly be administered over a period of up to 28 days following chemotherapy or bone-marrow transplant or until a platelet count of >20,000/mm$^3$, preferably >50,000/mm$^3$, is achieved. More commonly, TPO will be administered over one week or less, often over a period of one to three days. In general, a therapeutically effective amount of TPO is an amount sufficient to produce a clinically significant increase in the proliferation and/or differentiation of lymphoid or myeloid progenitor cells, which will be manifested as an increase in circulating levels of mature cells (e.g. platelets, erythrocytes, or neutrophils). Treatment of platelet disorders will thus be continued until a platelet count of at least 20,000/mm$^3$, preferably 50,000/mm$^3$ is reached. TPO can also be administered in combination with other cytokines such as IL-3, -6 and -11; stem cell factor; erythropoietin (EPO); G-CSF and GM-CSF. Within regimens of combination therapy, daily doses of other cytokines will in general be: EPO, ≦150 U/kg; GM-CSF, 5–15 µg/kg; IL-3, 1–5 µg/kg; and G-CSF, 1–25 µg/kg. Combination therapy with EPO, for example, is indicated in anemic patients with low EPO levels.

TPO can also be used ex vivo, such as in autologous marrow culture. Briefly, bone marrow is removed from a patient prior to chemotherapy and treated with TPO, optionally in combination with one or more other cytokines. The treated marrow is then returned to the patient after chemotherapy to speed the recovery of the marrow. In addition, TPO can be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy.

TPO is also useful as a laboratory reagent in the study of hematopoietic processes. The compositions and methods of the present invention provide storage-stable preparations of thrombopoietin for such uses.

The invention is further illustrated by the following, non-limiting examples.

EXAMPLES

Recombinant human and mouse TPO were prepared using transfected baby hamster kidney cells (BHK 570 cells; ATCC CRL 10314). TPO was purified from cell-conditioned culture media by affinity chromatography on immobilized MPL receptor or chromatographically using a combination of dye-ligand affinity chromatography, ion-exchange chromatography, and adsorption of protein contaminants on hydroxyapatite. Biological activity of TPO was assayed in a mitogenesis assay using BaF3 cells transfected with an expression vector encoding the human MPL receptor (Vigon et al., *Proc. Natl. Acad. Sci. USA* 89:5640–5644, 1992) as target cells. BaF3 is an interleukin-3 dependent pre-lymphoid cell line derived from murine bone marrow (Palacios and Steinmetz, *Cell* 41: 727–734, 1985; Mathey-Prevot et al., *Mol. Cell. Biol.* 6: 4133–4135, 1986). Cells were exposed to test samples in the presence of $^3$H-thymidine. The amount of $^3$H-thymidine incorporated into cellular DNA was quantitated by comparison to a standard curve of human TPO. 10 U/ml was defined as the amount giving half-maximal stimulation in the mitogenesis assay.

Polysorbate 80 (Tween 80), grade NF, was obtained from Spectrum Chemical Mfg. Corp., New Brunswick, N.J. Sodium chloride (AR, USP), sodium phosphate, dibasic, heptahydrate (USP, TAC), and sodium phosphate, monobasic, monohydrate (USP), were obtained from Mallinkrodt Chemical Corp., Chesterfield, Mo.

Example 1

Surface adsorption of purified thrombopoietin was evaluated by filter recovery and recovery from solutions incubated with glass beads. Samples of TPO were diluted in appropriate buffers (see Table) for testing.

TABLE

| TPO* | Buffer | Additives** |
|---|---|---|
| Mouse, chrom. | 20 mM citrate pH 4.0, 6.0 | — |
| Mouse, chrom. | 20 mM citrate pH 4.0, 6.0 | 0.25% HSA |
| Mouse, chrom. | 20 mM K phosphate pH 6.0, 8.0 | — |
| Mouse, chrom. | 20 mM K phosphate pH 6.0, 8.0 | 0.25% HSA |
| Mouse, chrom. | 20 mM Tris pH 8.0 | — |
| Mouse, chrom. | 20 mM Tris pH 8.0 | 0.25% HSA |
| Mouse, chrom. | — | mito diluent |
| Human, affin. | 20 mM citrate pH 4.0, 5.0, 6.0, 7.0, 8.0 | — |
| Human, affin. | — | mito diluent |
| Human, chrom. | 50 mM histidine pH 5.5 | — |
| Human, chrom. | 50 mM histidine pH 5.0 | 0.01% polysorbate 80 |
| Human, chrom. | 50 mM histidine pH 5.5 | 0.01% polysorbate 80 |
| Human, chrom. | 50 mM histidine pH 6.0 | 0.01% polysorbate 80 |
| Human, chrom. | 50 mM histidine pH 5.5 | 0.05% polysorbate 80 |
| Human, chrom. | 50 mM succinate pH 5.5 | 0.01% polysorbate 80 |
| Human, chrom. | 20 mM K phosphate pH 6.0 | — |
| Human, chrom. | 20 mM K phosphate pH 6.0 | 0.01% polysorbate 80 |
| Human, chrom. | 20 mM K phosphate pH 6.0 | 0.01% polysorbate 80 + 5% sucrose |
| Human, chrom. | 20 mM K phosphate pH 6.0 | 0.01% polysorbate 80 + 5% mannitol |

TABLE-continued

| TPO* | Buffer | Additives** |
|---|---|---|
| Human, chrom. | 20 mM K phosphate pH 6.0 | 0.01% polysorbate 80 + 1% PEG 3350 |
| Human, chrom. | 20 mM K phosphate pH 6.0 | 5% sucrose |
| Human, chrom. | 20 mM K phosphate pH 6.0 | 5% mannitol |
| Human, chrom. | 20 mM K phosphate pH 6.0 | 1% PEG 3350 |
| Human, chrom. | 20 mM K phosphate pH 6.0 | 0.13 M NaCl |
| Human, chrom. | 20, 50, 100 mM K phosphate pH 6.0 | 0.05% polysorbate 80 + 0.13 M NaCl |
| Human, chrom. | 20 mM K phosphate pH 4.0, 5.0, 6.5, 7.0, 8.0 | 0.05% polysorbate 80 + 0.13 M NaCl |
| Human, chrom. | 20 mM Na phosphate pH 5.0, 5.5, 6.0 | 0.05% polysorbate 80 + 0.14 M NaCl |
| Human, chrom. | 20 mM histidine pH 5.0, 5.5, 6.0 | 0.05% polysorbate 80 + 0.14 M NaCl |
| Human, chrom. | 20 mM Na phosphate pH 6.0 | 0.05% polysorbate 80 |
| Human, chrom. | 20 mM Na phosphate pH 6.0 | 0.14 M NaCl |
| Human, chrom. | 20 mM Na phosphate pH 6.0 | 0.14 M NaCl + 0.001%, 0.01%, 0.05% polysorbate 80 |
| Human, chrom. | 20 mM Na phosphate pH 6.0 | 0.14 M NaCl + 0.001%, 0.01%, 0.05% polysorbate 20 |

*chrom. = chromatographically purified; affin. = affinity purified.
**mito diluent = RPMI 1640 supplemented with 10% FBS, 1% L-glutamine, 1% PSN antibiotic mix (penicillin, streptomycin, neomycin), 0.001 M sodium pyruvate, 0.025 M Hepes, 0.00033% w/v mercaptoethanol.

Figure 1:
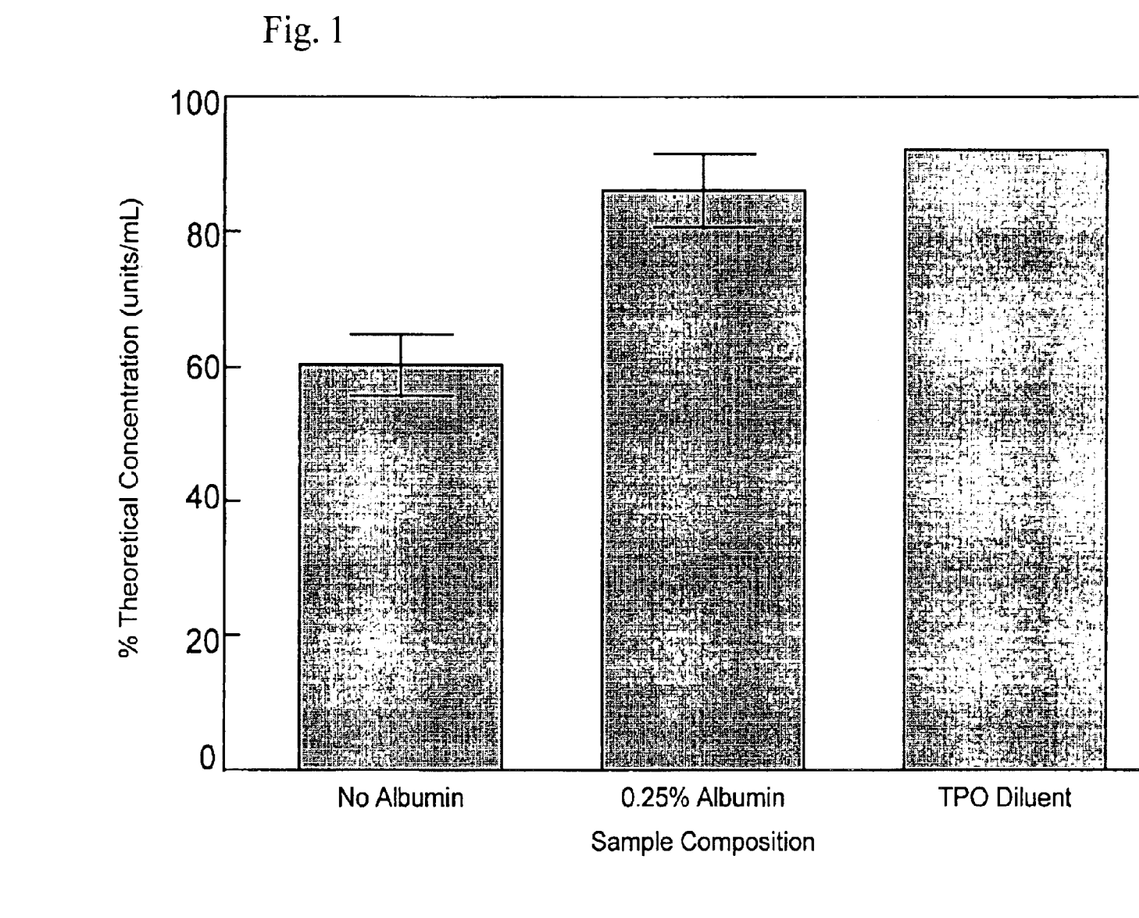
FIG. 1 illustrates the effects of albumin and serum proteins on recovery of recombinant mouse TPO after filtration.
Figure 2:
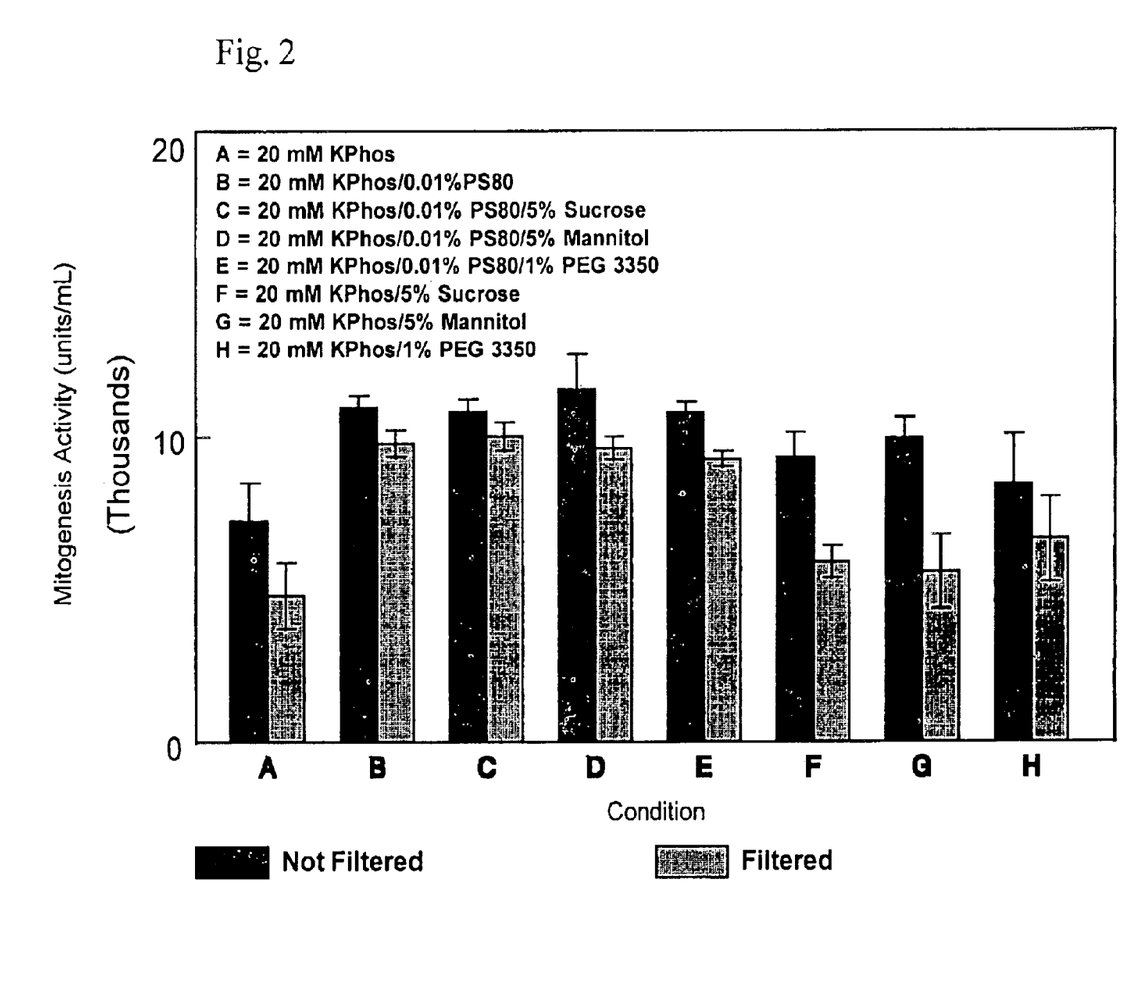
FIG. 2 illustrates the effects of non-ionic surfactants, polyols and sugar on recovery of recombinant human TPO after filtration.
Figure 3:
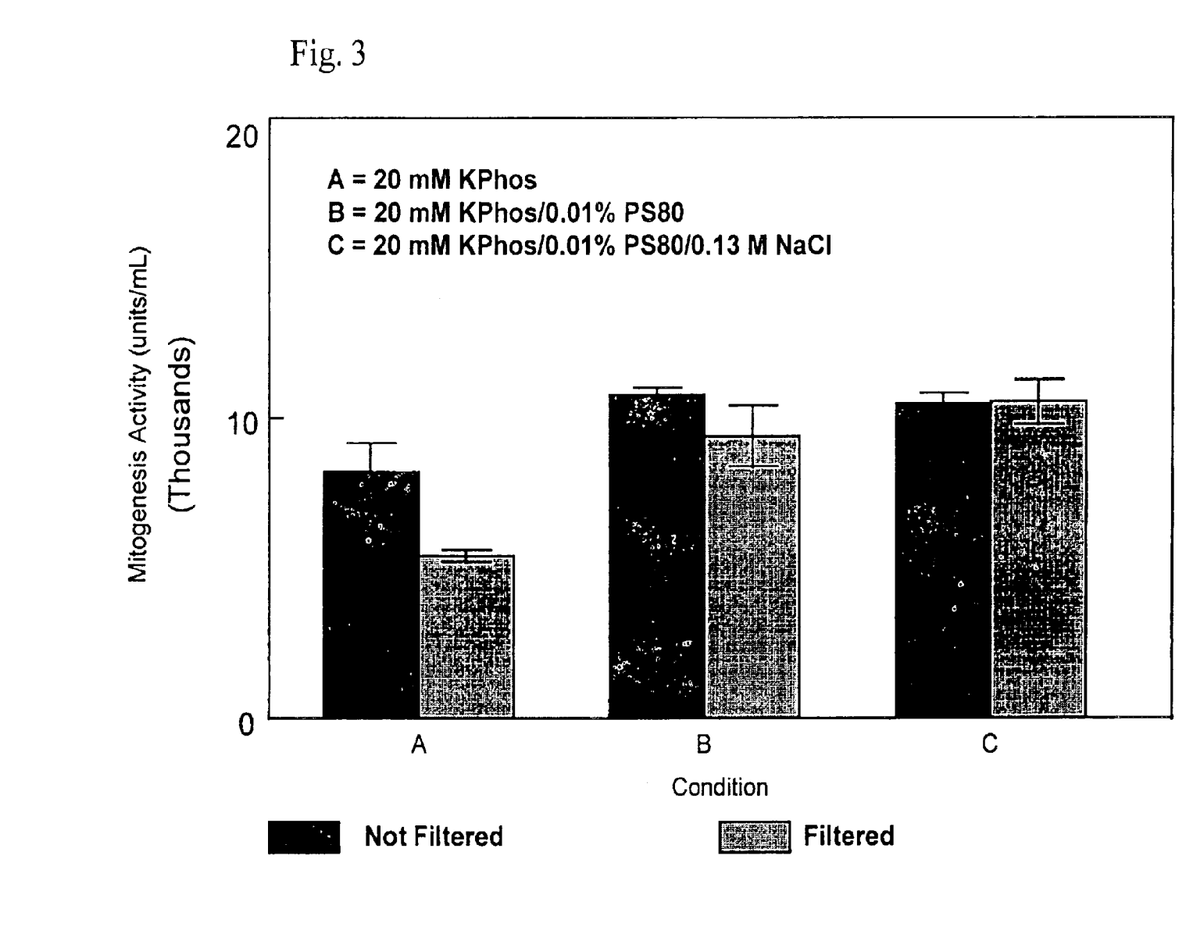
FIG. 3 illustrates the reduction of surface adsorption of TPO by NaCl.

Filter adsorption was measured using 0.2 μm polyvinylidene fluoride membrane filters (Durapore™ filters; Millipore, Bedford, Mass.) or Acrodisc™ membrane filters (Gelman Sciences, Ann Arbor, Mich.) attached to syringes. Solutions of TPO were pushed through the filters by hand. Samples were taken before addition of the solution to the syringe and after passage through the filter. Recovery of recombinant mouse TPO was found to be higher in formulations containing 0.25% human serum albumin than in those without albumin (FIG. 1). Similar results were obtained with recombinant human TPO. Large filter recovery differences were not observed as a function of pH over the range tested. (pH 4–8), but recovery was greatest at pH 6.0. Surface adsorption of recombinant human TPO was also reduced when 0.01% polysorbate 80 was included in the formulation (FIG. 2). Isotonic sodium chloride was found to further reduce adsorption in the presence of polysorbate 80 (FIG. 3).

Figure 4:
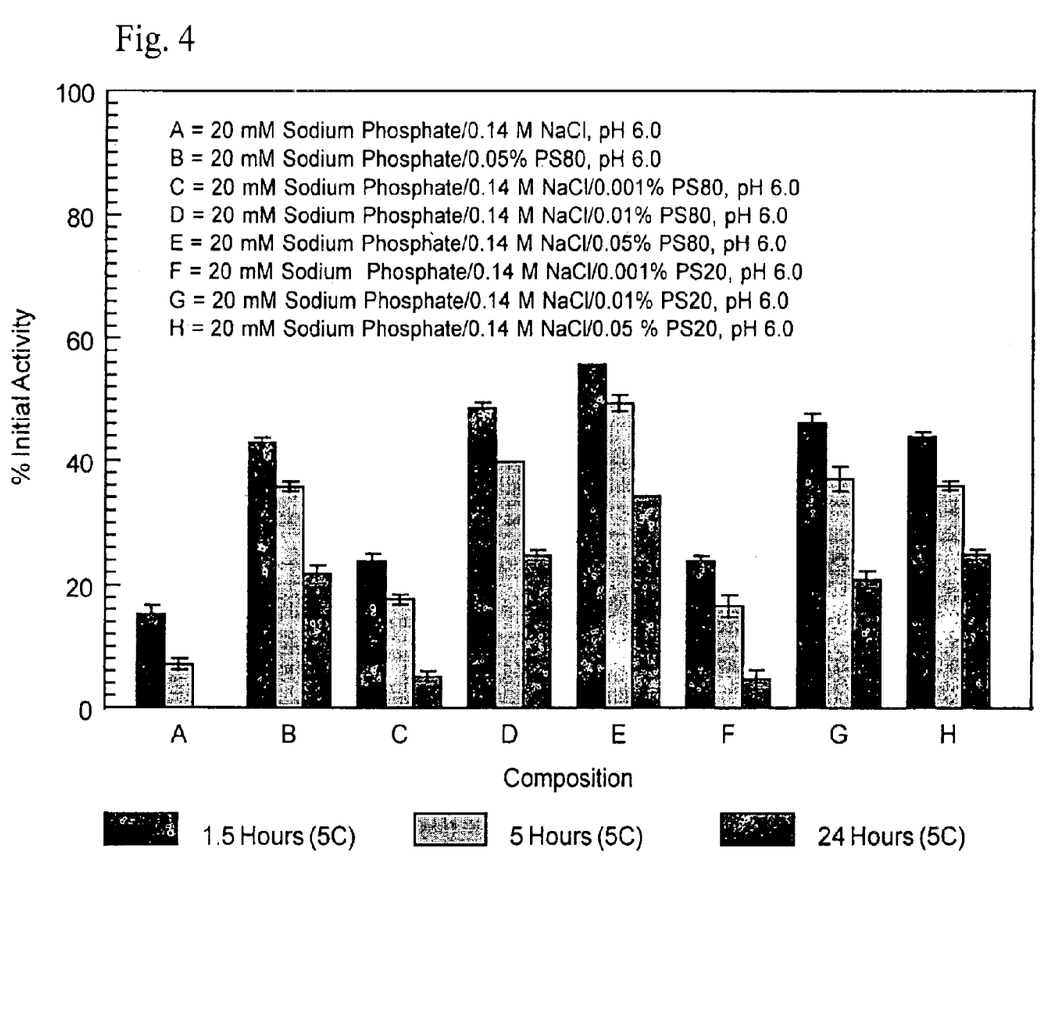
FIG. 4 illustrates the effects of various formulations on the adsorption of TPO to glass beads.

Surface adsorption was further investigated under exaggerated surface-to-volume ratios using glass beads. 0.5 ml samples of dilute TPO solutions (≈10 μg/ml) were exposed to 1.0 g of glass beads. (425–600 μm) at 5° C. on a tube rocker. Mitogenic activity was determined after 1.5, 5 and 24 hours to evaluate adsorption as a function of time. As shown in FIG. 4, adsorption increased with time over the 24-hour test period. Adsorption was reduced to a greater extent by polysorbate 80 than by polysorbate 20. Recovery increased as polysorbate 80 concentration was increased from 0.001% to 0.05%. The combination of polysorbate 80 and isotonic sodium chloride was more effective at reducing surface adsorption than was polysorbate 80 alone.

Example 2

The effect of pH on the stability of TPO in solution was tested in phosphate and histidine buffers. Samples of affinity and chromatographically purified recombinant mouse and human TPO were diluted in appropriate buffers or titrated with NaOH or HCl to the desired pH (see Table). The samples were then stored at various temperatures and assayed intermittently by mitogenesis assay as described above and SDS-polyacrylamide gel electrophoresis (SDS PAGE) followed by western blotting. Pseudofirst-order degradation rate constants ($K_{obs}$) were estimated from the slopes of log-linear fits of % mitogenic activity remaining vs. time, when appropriate.

SDS PAGE/western blot analysis showed that affinity-purified recombinant human TPO undergoes proteolysis to lower molecular weight variants in a pH- and time-dependent fashion. In the. pH range of 6–8, proteolysis resulted in cleavage to two lower molecular weight variants (35 and 18 kD by gel electrophoresis), with proteolysis increasing with increasing pH as a function of temperature. At pH≦5, a degradation product with an apparent molecular weight slightly lower than that of the parent protein (≈60 kD by gel electrophoresis) was evident, and increased with decreasing pH as a function of temperature.

Chromatographically purified recombinant human TPO showed a different degradation profile. SDS PAGE/western blot analysis indicated a temperature-dependent cleavage to two lower molecular weight species (30 and 20 kD by gel electrophoresis) at pH≦5, with proteolysis increasing with decreasing pH. Significant proteolysis was not observed at pH>6, however higher molecular weight aggregates formed at increasing pH and temperature. All degradation products had less biological activity than the parent protein. The pH-rate profiles (in $K_{obs}$ vs. pH) representing the pseudofirst-order degradation rates ($K_{obs}$) of the protein suggested differences in the relative degradation rates of the various pathways as a function of temperature. The profiles at 30° C. and 37° C. were similar and exhibited a pH of maximum stability ≈6. Although rapid loss of bioactivity occurred at pH>6, gross changes were not evident by SDS PAGE and western blotting. These results suggested that at pH>6 degradation primarily occurs via deamidation, oxidation, or some other mechanism not detectable by electrophoresis. The degradation rate at 5° C. was relatively constant at pH≦6, suggesting that the degradation pathway (s) in this pH range have a large activation energy (steep temperature dependence) and do not significantly contribute to the overall loss of TPO at this temperature.

Figure 5:
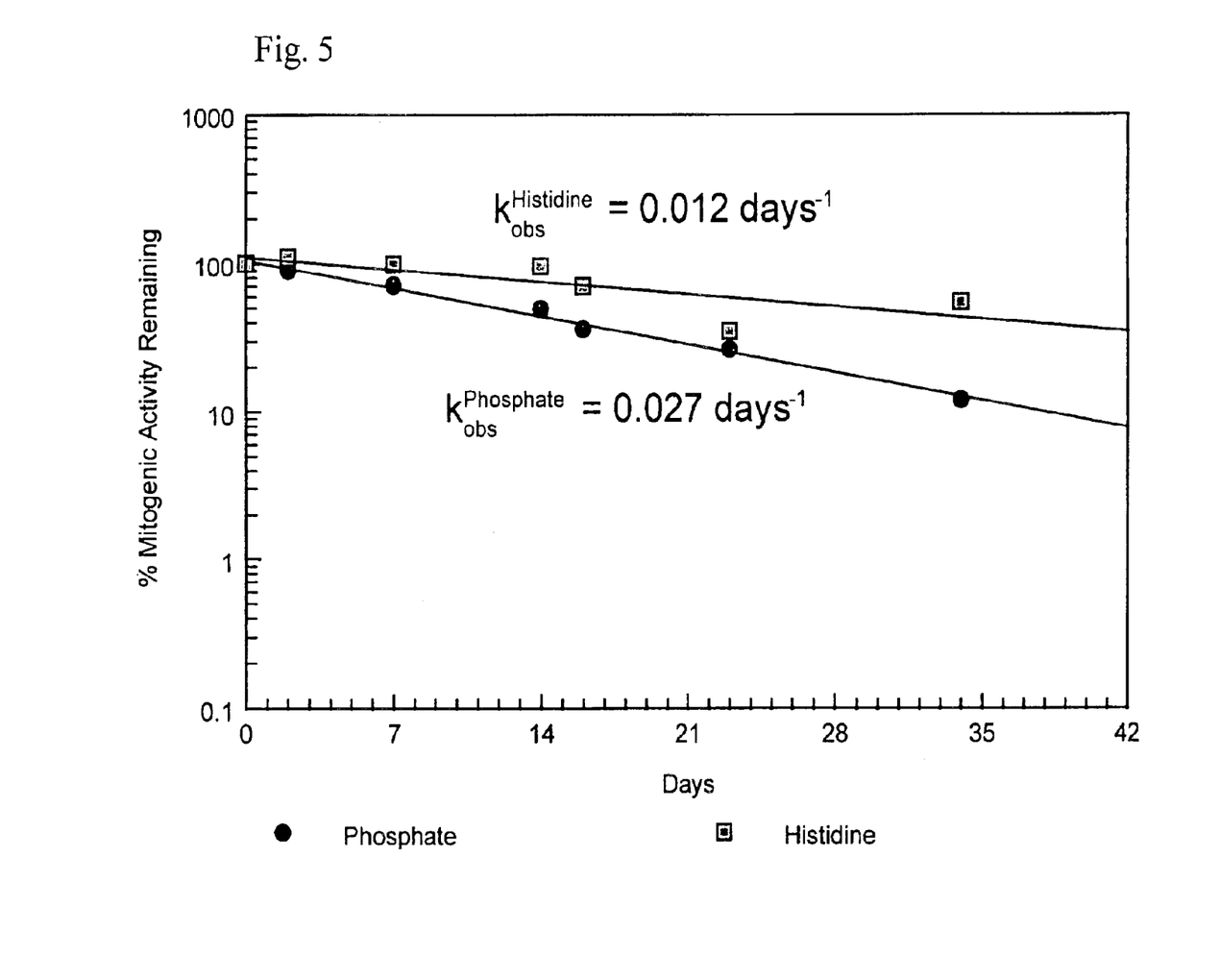
FIG. 5 is a plot of degradation profiles for chromatographically purified recombinant human TPO at 37° C. in 20 mM phosphate or histidine buffer at pH 6.0.

Equivalent degradation rates were found as a function of pH when results with sodium and potassium phosphate buffers were compared. Significant differences were not observed when different concentrations of potassium phosphate buffers were used (20 mM–100 mM, pH 6.0). However, differences were noted when histidine was used as a buffer (20 mM) in the pH range 5 to 6. The degradation rate at pH 5.0 was greater in histidine buffer than in phosphate buffer at 37° C., but at pH 5.5 or 6.0 the degradation rates were equivalent or lower in histidine buffer (FIG. 5). Similar results were seen at 30° C., although the distinctions were less profound. At 5° C. the degradation rates were equivalent in histidine and phosphate buffers at pH 5–6. These results are consistent with increased degradation via low pH degradation pathways in the presence of histidine, whereas histidine reduces degradation via high pH degradation pathways. Since the low pH degradation pathways are inhibited as temperature is decreased, the enhanced degradation in the presence of histidine is not evident at 5° C.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of stabilizing an aqueous solution of thrombopoietin comprising adding to said solution a stabilizing amount of histidine.

2. A method according to claim 1 wherein said stabilizing amount of histidine is 5–500 mM.

3. A method according to claim 2 wherein said stabilizing amount of histidine is 10–100 mM.

4. A method according to claim 3 wherein said stabilizing amount of histidine is about 20 mM.

5. An aqueous pharmaceutical composition comprising:
   thrombopoietin;
   10–100 mM phosphate buffer;
   0.01–0.05% (w/v) of polysorbate 80;
   an isotonic amount of sodium chloride; and
   water, said composition having a pH of 6.0±0.5.

6. The aqueous solution of claim 5 wherein the thrombopoietin is included at a concentration of 0.1–10 mg/ml.

7. The aqueous solution of claim 5 wherein the phosphate buffer is sodium phosphate buffer or potassium phosphate buffer.

8. The aqueous solution of claim 7 wherein the concentration of phosphate buffer is about 20 mM.

9. The aqueous solution of claim 7 further comprising histidine at a concentration of 5–500 mM.

10. The aqueous solution of claim 9 wherein the concentration of histidine is 10–100 mM.

11. The aqueous solution of claim 10 wherein the concentration of histidine is about 20 mM.

12. An aqueous solution of thrombopoietin comprising:
    thrombopoietin;
    water; and
    histidine, wherein histidine is present at a concentration of 5–500 mM.

13. The aqueous solution of claim 12 wherein the thrombopoietin is included at a concentration of 0.1–10 mg/ml.

14. The aqueous solution of claim 12 wherein the concentration of histidine is 10–100 mM.

15. The aqueous solution of claim 14 wherein the concentration of histidine is about 20 mM.

* * * * *